United States Patent [19]

Alper et al.

[11] Patent Number: 4,665,213

[45] Date of Patent: May 12, 1987

[54] PROCESS FOR THE PRODUCTION OF ESTERS

[75] Inventors: Howard Alper, Ottawa, Canada; David J. H. Smith, Camberley, England

[73] Assignee: The British Petroleum Company p.l.c., London, England

[21] Appl. No.: 899,919

[22] Filed: Aug. 25, 1986

[30] Foreign Application Priority Data

Aug. 29, 1985 [GB] United Kingdom ................. 8521547

[51] Int. Cl.⁴ ............................................. C07C 69/76
[52] U.S. Cl. .................................... 560/105; 560/204; 560/232; 560/233; 560/234; 560/114; 260/410; 562/406; 562/497; 562/522
[58] Field of Search ............... 560/105, 204, 232, 233, 560/234, 114; 260/410

[56] References Cited

U.S. PATENT DOCUMENTS

| | | | |
|---|---|---|---|
| 2,542,767 | 2/1951 | Gresham | 510/233 |
| 2,549,455 | 4/1951 | Gresham et al. | 560/233 |
| 2,612,520 | 9/1952 | Daumani et al. | 562/406 |
| 3,009,951 | 11/1961 | Kroeper et al. | 562/406 |
| 3,887,595 | 6/1975 | Nozaki | 562/406 |
| 4,013,583 | 3/1977 | Knifton | 562/406 |
| 4,209,467 | 6/1980 | Kojima | 560/233 |
| 4,301,090 | 11/1981 | Pesa et al. | 560/233 |
| 4,313,893 | 2/1982 | Pesa et al. | 560/233 |
| 4,331,612 | 5/1982 | Pesa et al. | 560/233 |
| 4,451,407 | 5/1984 | Pesa et al. | 560/233 |
| 4,558,153 | 12/1985 | Cook | 560/105 |
| 4,614,816 | 9/1986 | Drury et al. | 560/243 |
| 4,619,790 | 10/1986 | Kummer | 560/233 |

FOREIGN PATENT DOCUMENTS 0173019 3/1986 European Pat. Off. ............ 562/607

OTHER PUBLICATIONS

Bryant, F. J. et al, ACS Dir. Pet. Chem. 18,(1) Feb. 1977, pp. 193–195.

*Primary Examiner*—Paul J. Killos
*Attorney, Agent, or Firm*—Brooks, Haidt, Haffner & Delahunty

[57] ABSTRACT

Carboxylic acid esters are produced by reacting an olefinic hydrocarbon with an ester of formic acid in the presence of both carbon monoxide and oxygen at a temperature of up to 200° and a pressure of up to 300 bar in the presence of water, typically in an amount of from 0.01 to 5% w/w, a source of protons, which is preferably a mineral acid or a tectometallosilicate in the hydrogen form, and as catalyst (a) a source of palladium, and (b) a source of copper.

10 Claims, No Drawings

PROCESS FOR THE PRODUCTION OF ESTERS

The present invention relates to a process for the production of carboxylic acid esters by the reaction of a formic acid ester with an olefinic hydrocarbon.

The production of carboxylic acid esters by reacting an ester of formic acid with an olefin is known from, for example, EP-A-92350 and EP-A-106656.

EP-A-92350 discloses a homogeneous process for converting olefins to carboxylic acid esters by reacting an olefin with a formate ester with a soluble iridium catalyst and an iodide promoter at temperatures of from 150° to 300° C. in a carboxylic acid solvent. The process of EP-A-92350 does not require carbon monoxide or water and when oxygen is present it should only be maintained at low levels.

EP-A-106656 discloses a process for the production of a carboxylic acid ester by reacting at elevated temperature an ester of formic acid with an olefin in the presence, as catalyst, of a Group VIII noble metal, optionally in the presence of carbon monoxide. In this process the preferred Group VIII metal is iridium and it is preferred to employ a halide promoter. It is also preferred to employ a strong acid as a co-promoter. The process is preferably effected in the substantial absence of oxygen and the presence of carbon monoxide is not essential.

We have now found that by using a palladium/copper catalyst and a source of aqueous acid in the presence of both carbon monoxide and oxygen, the use of halid promoters, with their associated problems of corrosion and separation, can be avoided and that the process can be operated under substantially milder conditions than the prior art processes.

Accordingly, the present invention provides a process for the production of a carboxylic acid ester which process comprises reacting an olefinic hydrocarbon with an ester of formic acid in the presence of both carbon monoxide and oxygen at a temperature of up to 200° C. and a pressure of up to 300 bar in the presence of water, a source of protons and, as catalyst (a) a source of palladium and (b) a source of copper.

The process of the present invention is preferably carried out by reacting the olefinic hydrocarbon with the formic acid ester in the liquid phase under the conditions described above with the catalyst dissolved or suspended therein.

As regards the olefinic hydrocarbon feedstock this is suitably one or more linear or cyclic olefins having one or more carbon-carbon double bonds. Preferred olefins include $C_1$–$C_{20}$ aliphatic olefins, $C_4$–$C_{20}$ cyclic olefins and aromatic olefins. Most preferred olefins are $C_1$–$C_{12}$ aliphatic mono- and diolefins, $C_6$–$C_{10}$ cyclic olefins and styrene.

The formic acid ester is suitably an alkyl ester of formic acid and is preferably a $C_1$–$C_{12}$ alkyl ester. Preferred examples include methyl formate, ethyl formate, propyl formate, n-butyl formate, and the like.

The carboxylic acid ester produced by the process of the invention is one in which (i) the carboxylic acid group has one carbon atom more that the starting olefin and (ii) the ester group corresponds to that derived from the formic acid ester. Thus, if the olefin is ethylene and the formic acid ester used is methyl formate the carboxylic acid ester formed is methyl propioniate. Using higher mono-olefins, the possibility exists for the production of two or more carboxylic acid ester isomers. It is a feature of the present invention that under such circumstances the reaction is highly specific to the branched-chain ester. The reaction is completely regiospecific, or highly regioselective, when the formate is employed as both reactant and solvent. In the case of diolefins, such as 1,7-octadiene, both mono- and diesters are formed in contrast to the hydroesterification of olefins in alcohol under similar conditions, where only the diester is formed.

As regards the catalyst, this comprises a source of palladium and a source of copper. The sources of palladium and copper can be in any convenient form e.g. the finely divided metal, simple inorganic salts, as well as inorganic or organometallic complexes. For palladium, preferred sources are the simple inorganic salts such as the chloride or bromide and the nitrate. The copper source is also preferably a copper halide e.g. copper (II) chloride, copper(II)bromide, copper(I) chloride or copper (I) bromide.

The sources of palladium and copper are suitably present in amounts such that the molar ratio of olefin to palladium or copper is greater than 5:1.

The presence of water is essential to the operation of the process of the invention. Only trace amounts of water are necessary, typically of the order of from 0.01 to 5% w/w. For optimum operation of the process the presence of large amounts of water should preferably be avoided, otherwise side-reactions may occur.

The source of protons may suitably suitably by a mineral acid or an organic acid. Suitably the source of protons and water may be combined in the form of an aqueous acid, preferably an aqueous mineral acid, e.g. aqueous hydrochloric acid, aqueous sulphuric acid or aqueous hydrobromic acid, or the like. Alternatively, a solid source of protons, for example a hydrogen ion-exchanged tectometallosilicate or a hydrogen ion-exchanged layered clay may be employed. Suitable tectometallosilicates include the aluminosilicate zeolites, for example ZSM-5.

The process of the present invention is carried out in the presence of a gas mixture comprising carbon monoxide and oxygen. The carbon monoxide/oxygen mixture can be used to provide an overpressure for the process if the process is carried out at superatmospheric pressure. The carbon monoxide/oxygen gas mixture is suitably one having a molar ratio of carbon monoxide to oxygen in the range 5:1 to 1:5.

Although the process may be carried out at room temperature, elevated temperatures up to 200° C. can be used in order to accelerate the reaction. Preferably the reaction is carried out at a temperature in the range from 25° to 150° C. The reaction may also be carried out at atmospheric pressure or at a superatmospheric pressure of up to 300 bars. When a superatmospheric pressure is used it can be generated by the carbon monoxide and oxygen or by the further addition of an inert gas such as nitrogen, helium, argon or carbon dioxide.

As mentioned above, the process described hereinbefore can be carried out in the liquid phase using the reactants as the reaction medium. However, a solvent may optionally be used in order to dilute the reactants, to assist in solubilising the catalyst and to increase the reaction rate. A preferred solvent is dioxan, though other solvents such as dimethyl sulphoxide and glycol ethers may be used.

The process can be carried out either batchwise or continuously.

The invention will now be further illustrated by the following examples.

EXAMPLE 1

A mixture of palladium chloride [27 mg, 0.15 mmol] and $CuCl_2$ [41 mg, 0.30 mmol] in dioxane (10 ml) was stirred under carbon monoxide for 5 minutes. Then n-butyl formate (4 ml), 1-decene [0.75 g, 5.35 mmol] and aqueous hydrochloric acid (0.1 ml) were added and $CO/O_2$ (1:1) was bubbled through the solution at room temperature and atmospheric pressure for a period of 24 hours. Analysis of the product gave n-butyl 2-methyldecanoate and n-butyl undecanoate with respectively 87% and 13% selectivity with a 64% conversion of the formic acid ester.

EXAMPLE 2

Example 1 was repeated using the following reaction mixture:

$PdCl_2$: 54 mg, 0.30 mmol
$CuCl_2$: 202 mg, 1.5 mmol
HCL: 0.2 ml
Dioxan: 10 ml
$HCOOC_4H_9$: 4 ml
1-decene: 0.75 g, 5.35 mmol After two days reaction 98% of the formic acid ester had been converted with a 71.9% selectivity to n-butyl 2-methyldecanoate and a 15.7% selectivity to n-butyl undercanoate.

COMPARISON TEST A

The procedure of Example 1 was repeated except that the reaction was carried out in a closed system initially charged with a $CO/O_2$ mixture, i.e. $CO/O_2$ was not bubbled through the reaction mixture. The reaction ceased after limited conversion.

This test demonstrates the importance of carrying out the reaction in the presence of both carbon monoxide and oxygen.

COMPARISON TEST B

The procedure of Example 1 was repeated except that oxygen was excluded from the reaction mixture. Only traces of ester were detected.

The test was repeated using excess $CuCl_2$. Again only traces of the ester were detected.

This test demonstrates that the presence of oxygen is essential for the performance of the invention.

COMPARISON TEST C

The procedure of Example 1 was repeated except that copper was omitted as a component of the catalyst system. No reaction occurred.

This test demonstrates that under the mild reaction conditions of Example 1 copper is an essential component of the catalyst system.

EXAMPLE 3

The procedure of Example 1 was repeated except that instead of copper chloride there was used copper acetate.

71% esters in a 6:1 ratio of branched:linear isomers were obtained.

EXAMPLE 4

The procedure of Example 1 was repeated except that instead of copper chloride there was used copper triflate.

After 28 hours 20% esters were obtained.

EXAMPLE 5

The procedure of Example 1 was repeated except that labelled carbon monoxide ($^{13}CO$) was employed. Ester was obtained from the olefin with greater than 99% of the label located at the carbonyl carbon. This means that the ester carbonyl group arises from CO and not from the formate reactant.

EXAMPLE 6

The procedure of Example 1 was repeated except that 1,7-octadiene was used in place of 1-decene. Both mono- and di-esters were formed in a 2:1 ratio.

We claim:

1. A process for the production of a carboxylic acid ester which process comprises reacting an olefinic hydrocarbon with an ester of formic acid in the presence of both carbon monoxide and oxygen at a temperature of up to 200° C. and a pressure of up to 300 bar in the presence of water, a source of protons and, as catalyst (a) a source of palladium and (b) a source of copper.

2. A process according to claim 1 wherein the unsaturated hydrocarbon is reacted with the ester of formic acid in the liquid phase with catalyst dissolved or suspended therein.

3. A process according to claim 1 wherein the olefinic hydrocarbon is a $C_1$–$C_{20}$ aliphatic olefin, a $C_4$–$C_{20}$ cyclic olefin or an aromatic olefin.

4. A process according to claim 1 wherein the ester of formic acid is a $C_1$–$C_{12}$ alkyl ester.

5. A process according to claim 1 wherein water is present in an amount in the range from 0.01 to 5% w/w.

6. A process according to claim 1 wherein the source of protons is either a mineral acid or an organic acid.

7. A process according to claim 6 wherein the source of protons is an aqueous mineral acid.

8. A process according to claim 1 wherein the source of protons is either a hydrogen ion-exchanged tectometallosilicate or a hydrogen ion-exchanged layered clay.

9. A process according to claim 1 wherein the molar ratio of carbon monoxide to oxygen is in the range from 5:1 to 1:5.

10. A process according to claim 1 wherein the reaction is carried out at a temperature in the range from 25° to 150° C.

* * * * *

UNITED STATES PATENT AND TRADEMARK OFFICE
CERTIFICATE OF CORRECTION

PATENT NO. : 4,665,213

DATED : May 12, 1987

INVENTOR(S) : Howard Alper et al

It is certified that error appears in the above-identified patent and that said Letters Patent is hereby corrected as shown below:

Col. 1, line 62 "that" should read -- than --

Col. 2, line 29 "suitably suitably" should read -- suitably be --

Col. 3, line 32 "undercanoate" should read -- undecanoate --

Signed and Sealed this

Third Day of November, 1987

Attest:

DONALD J. QUIGG

Attesting Officer

Commissioner of Patents and Trademarks